US009162106B1

(12) United States Patent
Scheiman

(10) Patent No.: US 9,162,106 B1
(45) Date of Patent: Oct. 20, 2015

(54) ANKLE AND FOOT EXERCISE APPARATUS

(75) Inventor: Donald R. Scheiman, Sunnyvale, CA (US)

(73) Assignee: ADAPTable Products, Inc., Mountain View, CA (US)

( * ) Notice: Subject to any disclaimer, the term of this patent is extended or adjusted under 35 U.S.C. 154(b) by 445 days.

(21) Appl. No.: 13/507,420

(22) Filed: Jun. 25, 2012

Related U.S. Application Data

(60) Provisional application No. 61/571,677, filed on Jun. 30, 2011.

(51) Int. Cl.
*A63B 23/08* (2006.01)

(52) U.S. Cl.
CPC .................................... *A63B 23/08* (2013.01)

(58) Field of Classification Search
CPC ........ A63B 22/18; A63B 22/16; A63B 21/02; A63B 21/023; A63B 21/028; A63B 21/04; A63B 21/055; A63B 21/0552
USPC ............................................ 482/146, 79, 80
See application file for complete search history.

(56) References Cited

U.S. PATENT DOCUMENTS 3,421,760 A * 1/1969 Freeman, Jr. .................. 482/80
4,037,835 A * 7/1977 Forsyth .......................... 482/27
4,159,111 A * 6/1979 Lowth ............................ 482/80
4,629,181 A * 12/1986 Krive ............................. 482/71
5,823,975 A * 10/1998 Stark et al. .................... 600/595
6,821,235 B1 * 11/2004 Johnson et al. ................ 482/79

* cited by examiner

*Primary Examiner* — Loan H Thanh
*Assistant Examiner* — Rae Fischer
(74) *Attorney, Agent, or Firm* — Tom M. Moran

(57) ABSTRACT

An apparatus useful for performing foot and ankle exercises as part of a strengthening or rehabilitation program includes a foot platform positioned between an upper horizontal bar connected through a vertical assembly to a base frame adapted to sit in a stable position on a floor. The foot platform has an upper side to receive the user's foot and a lower side that pivotably engages through a fixed ball joint with the base frame to allow the user of the apparatus to exercise his or her ankle in all six movement directions without moving the leg. Resistance bands connect the foot platform to various points on the apparatus to provide a mechanism for resistance during exercise. The apparatus may be associated with a sensor on the foot platform that senses the position or movement of the foot in use and produces data regarding the exercise that is communicated to the user.

6 Claims, 10 Drawing Sheets

1
2
3
4
6
7
8
9
11
13
15
16
17
18
19
20
21
22
23
24
25
30
34
35

1
2
3
4
5
6
7
8
9
10
11
12
13
14
15
16
20
21
22
23
27
30
35

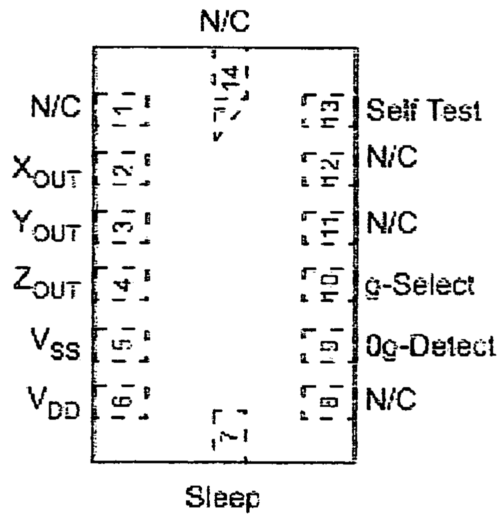

Figure 6

| Left pin name | Pin | Pin | Right pin name |
|---|---|---|---|
| (PCINT14/RESET) PC6 | 1 | 28 | PC5 (ADC5/SCL/PCINT13) |
| (PCINT16/RXD) PD0 | 2 | 27 | PC4 (ADC4/SDA/PCINT12) |
| (PCINT17/TXD) PD1 | 3 | 26 | PC3 (ADC3/PCINT11) |
| (PCINT18/INT0) PD2 | 4 | 25 | PC2 (ADC2/PCINT10) |
| (PCINT19/OC2B/INT1) PD3 | 5 | 24 | PC1 (ADC1/PCINT9) |
| (PCINT20/XCK/T0) PD4 | 6 | 23 | PC0 (ADC0/PCINT8) |
| VCC | 7 | 22 | GND |
| GND | 8 | 21 | AREF |
| (PCINT6/XTAL1/TOSC1) PB6 | 9 | 20 | AVCC |
| (PCINT7/XTAL2/TOSC2) PB7 | 10 | 19 | PB5 (SCK/PCINT5) |
| (PCINT21/OC0B/T1) PD5 | 11 | 18 | PB4 (MISO/PCINT4) |
| (PCINT22/OC0A/AIN0) PD6 | 12 | 17 | PB3 (MOSI/OC2A/PCINT3) |
| (PCINT23/AIN1) PD7 | 13 | 16 | PB2 (SS/OC1B/PCINT2) |
| (PCINT0/CLKO/ICP1) PB0 | 14 | 15 | PB1 (OC1A/PCINT1) |

Figure 7

ANKLE AND FOOT EXERCISE APPARATUS

REFERENCE TO OTHER APPLICATIONS

This application claims priority to U.S. Provisional Application 61/571,677 filed on Jun. 30, 2011 entitled Foot and Ankle Exercise Apparatus, Donald R. Scheiman inventor, which is incorporated in its entirety herein by reference.

FEDERALLY SPONSORED RESEARCH

This invention was not developed with any federally sponsored research or development money.

FIELD OF THE INVENTION

This invention relates to an apparatus useful for performing foot and ankle exercises as part of a strengthening or rehabilitation program.

PRIOR ART

Patents that relate to the field of invention include the following U.S. Pat. Nos. 4,605,220; 5,368,536; 6,277,057; 6,283,897; 6,821,235; 7,192,410; 7,322,914; and 7,794,367.

SUMMARY OF THE INVENTION

One aspect of this invention is an apparatus, that is, an article of manufacture or device, for exercising a human's foot or ankle. The apparatus comprises (a) a base frame adapted to sit in a stable position on a floor; b) a horizontal bar positioned above the base frame; c) a vertical assembly connecting the horizontal bar to the base frame; (d) a platform positioned between the horizontal bar, vertical assembly, and base frame, said platform having an upper side and a lower side, the upper side defining a forefoot region and a heel region for receiving a human foot; (e) a support member pivotably engaged with the lower side of the platform and attached to the base assembly; (f)) upper resistance connector for connecting the forefoot region of the platform to the horizontal bar and at least two resistance connectors for connecting the lateral and medial sides of the forefoot region to the vertical assembly or base frame; and (g) a lower resistance connector for connecting the platform to the base frame. Resistance connectors are then connected to the resistance connector attachments located on the platform to restively connect the platform on which the user's foot is positioned to the connector attachments of the base, the horizontal bar, and the vertical assembly. This allows the user of the invention to exercise his or her ankle in all six movements.

Another aspect of this invention is the combination of the apparatus described above with a sensor that senses the position or movement of such device in use and produces data regarding the exercise that is communicated to the user. The apparatus may further includes an electronic device for transmitting such data to a data receiving device that can store and process such data and may further include a browser based web service or client-server application interface to allow the user to evaluate information about the progress of his or her rehab exercise program.

Another aspect of this invention is a method for strengthening an ankle. The method comprises a) providing an exercise apparatus of claim described herein; b) placing a foot onto the platform of the exercise apparatus; and c) flexing the foot against the resistance provided by the apparatus.

Another aspect of this invention is a process of manufacture of an apparatus for exercising a human's foot or ankle, which process comprises a) providing a base frame adapted to sit in a stable position on a floor;
b) providing a horizontal bar for positioning above the base frame;
c) connecting a vertical assembly to the horizontal bar and to the base frame;
d) positioning a platform between the horizontal bar, vertical assembly, and base frame, said platform having an upper side and a lower side, the upper side defining a forefoot region and a heel region for receiving a human foot;
e) attaching a support member to the base frame assembly in a manner to pivotably engage with the lower side of the platform;
f) providing an attachment for a resistance connector to connect the forefoot region of the platform to the horizontal bar and at least two attachments to connect resistance connectors for connecting the lateral and medial sides of the forefoot region to the vertical assembly or base frame, and
g) providing an attachment for connecting a lower resistance connector to the heel region of the platform to the base frame.

A further step in such process is to include a sensor with the apparatus that senses the position or movement of such device in use and produces data regarding the exercise that is communicated to the user.

Other aspects of the invention will be apparent to one of ordinary skill in the art upon reading the following detailed description of this invention.

FIGURES

FIG. 6 is a schematic of the MMA7361, a representative accelerometer useful as a sensor in this invention for placement on the toe end of the foot placement platform to measure displacement.

FIG. 7 is a schematic of the Atmel Corporation AtMega328 microcontroller, which is used with the MMA7361 and programmed by the Arduino integrated drive electronics (ICE).

DEFINITIONS

Figure 1:
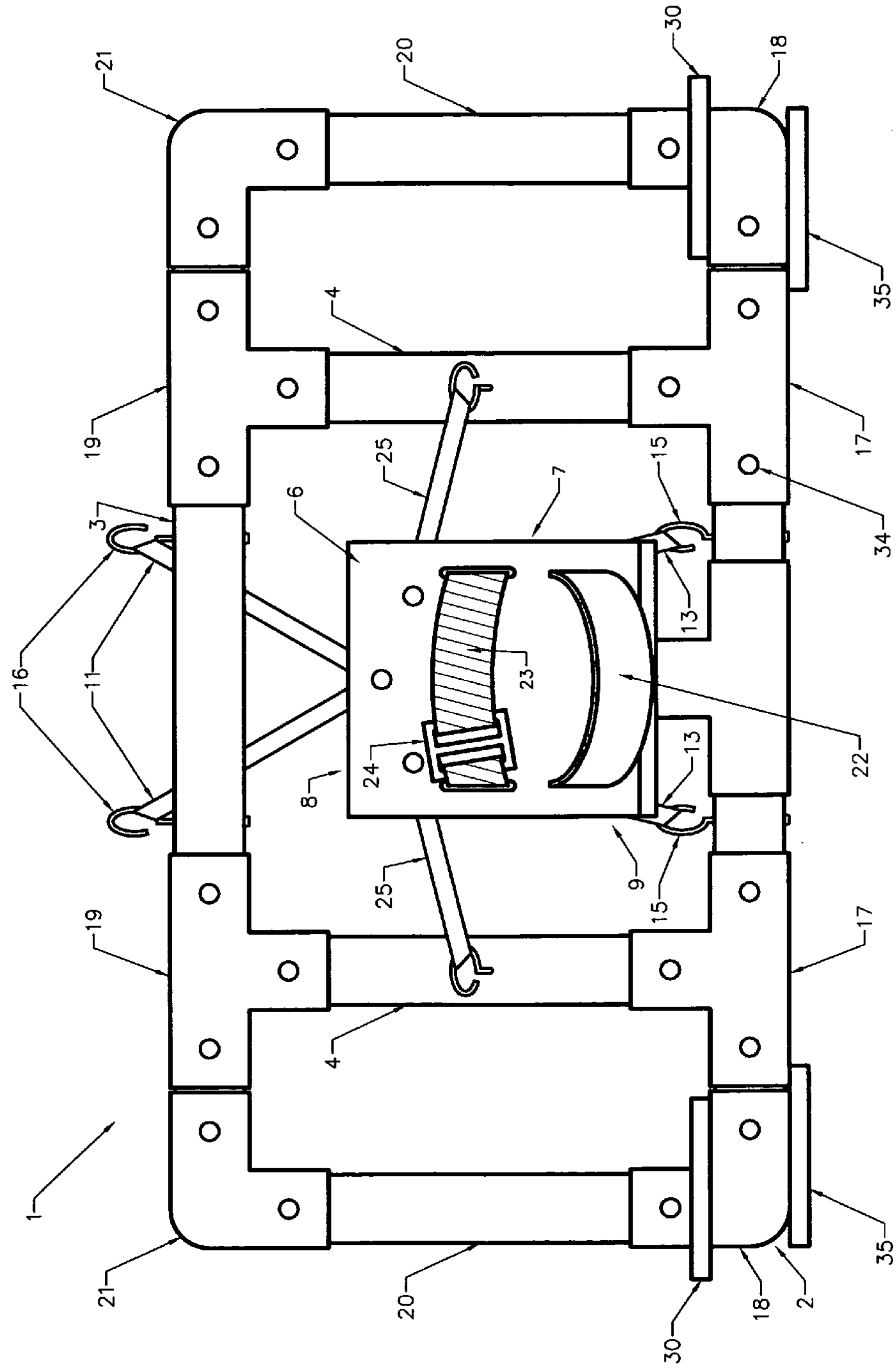
FIG. 1 is a flat, frontal view of one aspect of this invention shown without three dimensional perspectives.

For purposes of this patent application definition of terms used are those used in standard texts regarding exercise, rehabilitation, medicine, mechanical engineering, and electrical engineering and are available to those of ordinary skill in these arts. Other terms can be found in regular dictionaries, whether on line or in paper versions.

DETAILED DESCRIPTION

One aspect of this invention is an article of manufacture, that is, an apparatus or device, for exercising a human's foot or ankle. The apparatus comprises (a) a base frame adapted to sit in a stable position on a floor; b) a horizontal bar positioned above the base frame; c) a vertical assembly connecting the horizontal bar to the base frame; (d) a platform positioned between the horizontal bar, vertical assembly, and base frame, said platform having an upper side and a lower side, the upper side defining a forefoot region and a heel region for receiving a human foot; (e) a support member pivotably engaged with the lower side of the platform and attached to the base assembly; (f) upper resistance connector for connecting the forefoot region of the platform to the horizontal bar and at least two resistance connectors for connecting the lateral and medial sides of the forefoot region to the vertical assembly or base frame; and (g) a lower resistance connector for connecting the platform to the base frame. Resistance connectors are joined to the resistance connector attachments located on the platform to restively connect the platform on which the user's foot is positioned to the connector attachments of the base, the horizontal bar, and the vertical assembly. This allows the user of the invention to exercise his or her ankle in all six directions.

In reviewing the ankle rehabilitation and strengthening devices described in the art or available commercially I found that there was no single device that easily allowed a user to exercise his or her ankle in all six movements or directions in a single apparatus. The directions are abduction (moving the toes of the foot away from the median, i.e. central, plane of the body; eversion), adduction (moving the toes toward the median plane of the body; inversion), pronation (to raise the lateral, i.e. side or away from the median, edge of the foot), supination (to raise the medial edge of the foot), plantar flexion (turning the toes toward the sole of the foot), and dorsi-flexion (turning the toes upward toward the shin). Each of these movements will exercise a different set of muscles influencing ankle movement. Examples of the muscles exercised using the apparatus of this invention are exemplified in the following lists. For plantar flexion: soleus, gastrocnemius, flexor hallucis longus, flexor digitorum longus, plantar flexor, tibialis posterior, and peroneus longus and brevis. For dorsi-flexion: peroneus tertius, extensor digitorum longus, extensor hallucis longus, and tibialis anterior. For eversion (abduction and supination): peroneus longus and brevis, peroneus tertius, and extensor digitorum. For inversion (adduction and pronation): flexor hallucis longus, flexor digitorum longus, extensor hallucis longus, tibialis anterior, and tibialis posterior.

Referring to FIG. 1, one sees a frontal, non-perspective view of one aspect of an apparatus of this invention 1 for exercising a human's foot or ankle. The base frame 2 is adapted to sit in a stable position on a floor. A horizontal bar 3 is positioned above the base frame and is stably connected to a vertical assembly 4 connecting the horizontal bar 3 to the base frame 2. The vertical assembly may be designed to be structurally strong enough to accept the force provided by the resistance connectors. In the FIGS. 1-4, the vertical assembly is shown to have four arms to provide such strength, but it will be apparent to one of skill in the art that other designs may be employed on the full description is read and understood. A platform 5 is positioned between the horizontal bar 3, vertical assembly 4, and base frame 2, said platform 5 having an upper side 6 and a lower side 7 (not shown in this FIG. 1); the upper side 6 has a forefoot region 8 and a heel region 9 for receiving a human foot onto the upper side 6. A support member 10 (not shown in this FIG. 1) pivotably engages with the lower side 7 of the platform 5 and is attached to the base assembly 2. The pivotal engagement allows for rotation of the platform 5 in the X, Y, and Z axes of the apparatus. The engagement that allows for such rotation may be a ball joint or a universal join or an equivalent. Generally an extension from the lower side 7 of platform 5 engages with the extension 10 to form the ball joint or universal joint to provide the desired rotation. The at least one upper resistance connector 11 (two are shown in FIG. 1) connects between an attachment 12 (not shown in this FIG. 1) on the underside 7 forefoot region 8 of base 5 to an attachment 16 positioned above the platform and connected to the horizontal bar 3 or the vertical assembly 4. The attachment 12 may alternatively be attached to the end of the fore foot region 8 or even at the upper surface 6 of the fore foot region 8 of platform 5. At least two resistance connectors 25 connect the right and left sides (i.e. medial and lateral) of the forefoot region to attachments on the vertical assembly 4 (shown) or base frame, not shown. A lower resistance connector 13 secures an attachment means 14 (not shown in this FIG. 1) connected to the lower side 7 of platform 5 at the heel region to an attachment means 15 connected to the base frame 2. In FIG. 1 two resistance connectors and two hooks are shown. The attachment means are shown as hooks that can be screwed into the frame at a position as needed, but other equivalents such as a notch, a hole, or the like may be employed.

The base frame 2 may be made from a single piece of material such as plastic, metal, wood, or similar material that is stable and rigid. In the aspect shown in FIG. 1 and other Figures in this application, the base frame 2 is made of a tubular plastic such as furniture grade PVC and employs T joints 17 to connect to the vertical assembly 4, which in turn connects to the upper horizontal bar 3 by T joints 19. Additional vertical connectors 20 provide greater stability for the apparatus. The corners of the base may be connected using L joints 18 that are common in the art, while L joints 21 may be used to connect vertical pieces 20 to the horizontal bar 3. The tubular plastic may be friction fitted together, may be screwed together, or small screws 34 (represented by small circles in FIG. 1) may be used to screw the sections together and thus provide greater stability. In some cases, it may be useful to provide non-skid pads 35 to the bottom the base frame to prevent movement of the apparatus relative to the floor when in use. Such pads may be of the Velcro brand that would prevent sliding movement on a rug or they may be of a sticky surface for use on tile, wood, or other smooth type floors.

The upper surface 6 of platform 5 may be smooth or preferably may further comprise a non-skid or textured surface. The upper surface 6 of the platform 5 may further comprise at least one strap 23 for securing the foot to the platform 5. Such strap may employ a hook and loop fastener (e.g. Velcro brand) to aid in securing the foot the platform or may employ a buckle 24 as shown in FIG. 1 or other type of fastener such as a button, snap or other similar devices useful for securing the foot to the platform. The upper surface 6 may also include a heel stop 22 at the heel region 9 of platform 5 for limiting the motion of the heel relative to the platform. The design of the heel stop may be a ridge as shown in FIG. 1 or may be of a design shown in FIG. 5, as discussed in more detail hereinafter. The heel stop is used to secure the heel to the upper surface 6 of platform 5 and prevent the heel from moving laterally or medially doing the exercises using the apparatus of this invention.

A resistance connector (i.e., resistance means) useful in the apparatus of this invention may be any means that provides resistance to a particular movement when employed in the device of this invention. As shown in FIG. 1, the means 11, 13, and 25 is simply a stretchable band made of a plastic, rubber, or the like. Alternatively, it may be a spring, a hydraulic tube, bungee cord (i.e., a shock cord) having connector hooks at each end, or any other material that provides resistance to motion of the platform relative to the frame. In operation the user can strengthen her or his ankle by placing a foot onto the platform of the exercise apparatus and flexing the foot against the resistance provided by the apparatus. The resistance means is positioned to connect the platform to the upper horizontal bar, the vertical assembly and the base frame to allow the user to strengthen the various muscles of the foot, ankle and lower leg so that the movement can be in all directions needed for the full range of strengthening and rehab. The flexing includes abduction (moving the toes of the foot away from the median plane of the body), adduction (moving the toes toward the median plane of the body; inversion), pronation (eversion and abduction to raise the lateral edge of the foot), supination (inversion and abduction to raise the medial edge of the foot), plantar flexion (turning the toes toward the sole of the foot), and dorsi-flexion (turning the toes upward toward the shin). By attaching the forefoot region 8 through upper resistance means that are attached to opposite lateral sides of the platform and to the forefoot region of platform 5 to the upper horizontal bar 3, resistance for the plantar flexion movement is achieved. By attaching the forefoot region 8 of platform 5 to the vertical assembly at the 45 degree support 4 in FIGS. 1 and 2 or at the 90 degree support 20 in FIG. 2 (e.g., at least two attachments means for receiving the resistance means are independently positioned on separate arms of the vertical apparatus) resistance for the adduction and abduction, as well as pronation and supination, is achieved. By attaching the forefoot region 8 of platform 5 to the center of the base in FIG. 3, resistance for dorsi-flexion is achieved. One of ordinary skill will recognize that the exact positioning of the points of attachment and the resistance connectors can vary and still retain the utility of the apparatus.

The user can stand or sit while doing the exercise. In either case it may be useful to include foot rests 30 for receiving a left or right foot that is not being exercised, wherein the foot rests are attached to or are integral with the base frame. The foot rests 30 may be parallel to the floor for a standing use of the device or at an angle (e.g., about 45 degrees) to accommodate a sitting user. It is useful in carrying out the exercise using this invention to have a foot rest 30 that may vary in height. In some case the upper surface of the foot rest 30 may be at the level shown in FIG. 2 or may be at a level that approximates the height of the center of the upper side of platform 5. The higher level provides for greater stability for the user if both feet are positioned about the same distance from the floor, thus keeping the hips level relative to each other. Thus, the apparatus may come with foot rests that are removable from the base frame wherein the foot rests vary in height: one pair of foot rests would have a height as shown in FIGS. 1 and 2, while a second footrest would be of a vertical thickness that would be at the level shown or may be at a level that approximates the height of the center of the upper side of platform 5.

Figure 4:
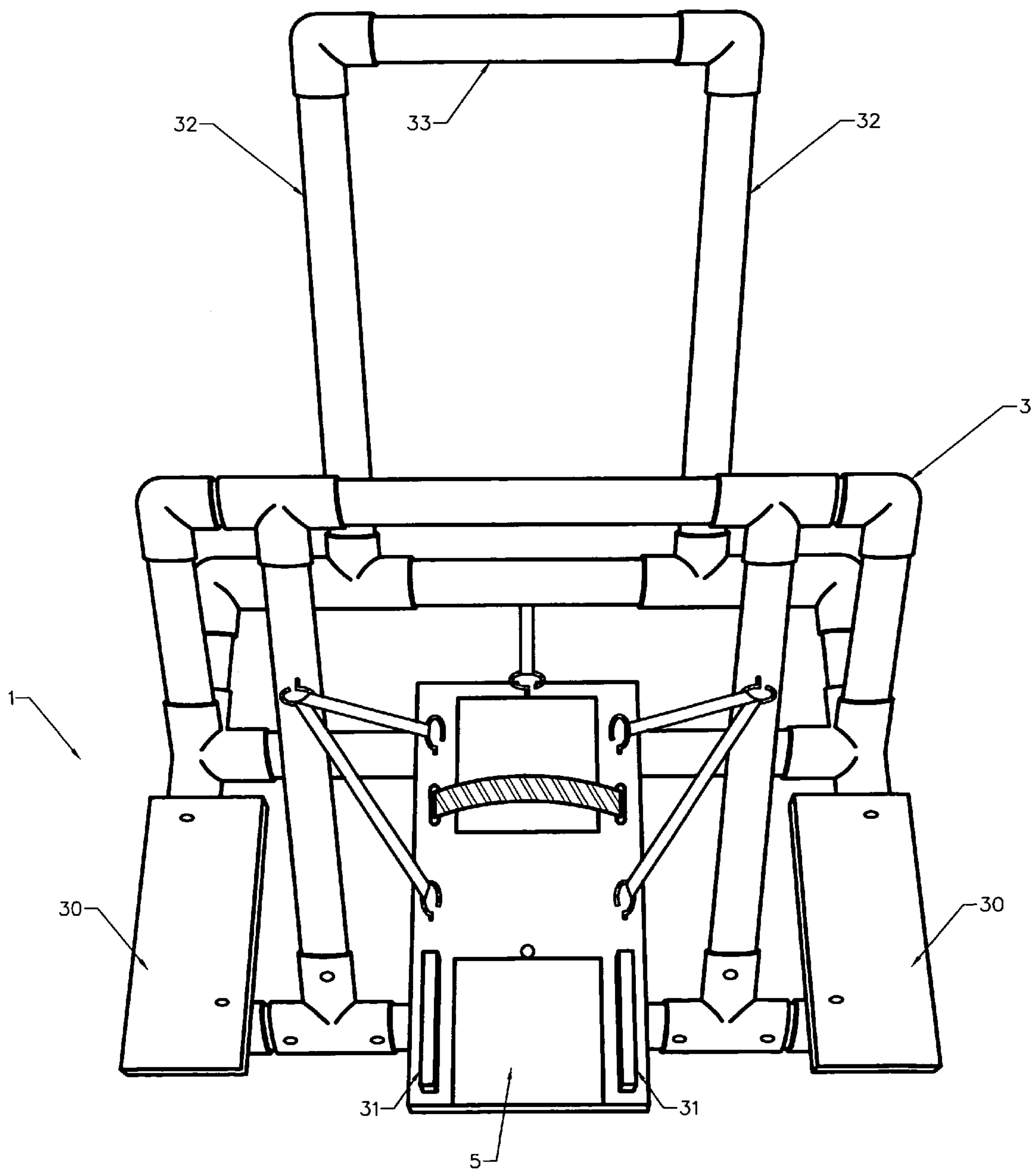
FIG. 4 is a perspective, photographic view of one aspect of an apparatus of this invention sitting in a stable position on a floor.

To aid the user if he or she wishes to stand while exercising the apparatus may include vertical, transverse arms spaced parallel to one another (not shown in FIG. 1, but see FIG. 4) and associated with or attached to the base frame at one end and a handle at the other end for receiving a user's hand to assist in balancing when the apparatus is in use. The stabilizing support may be integrated into the apparatus as shown in FIG. 4 or may be separate from the apparatus and may be free standing on the floor near the invention or attached to a wall or ceiling.

Figure 2:
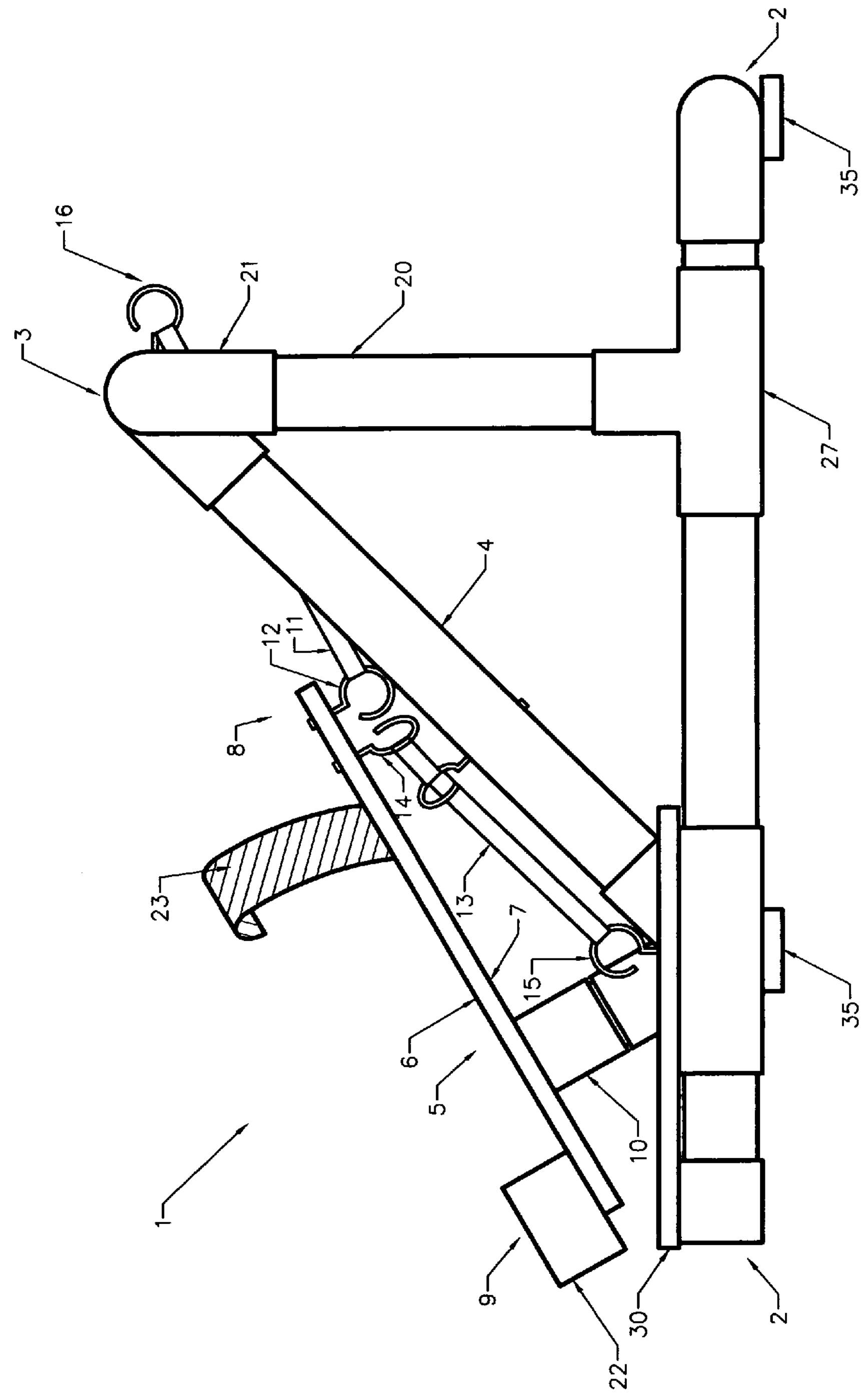
FIG. 2 is a side, non-perspective view of one aspect of an apparatus of this invention 1 for exercising a human's foot or ankle.
Figure 3:
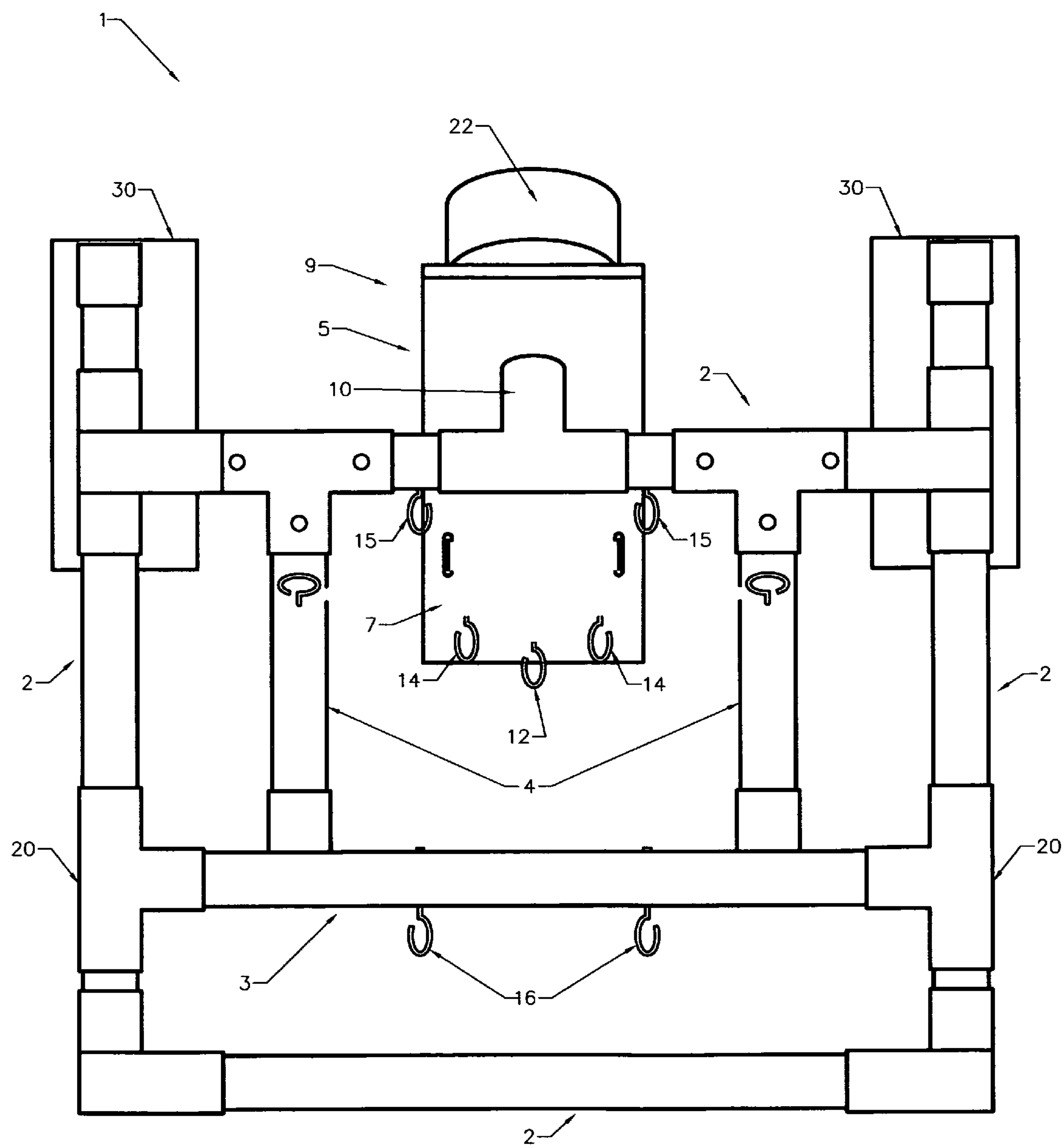
FIG. 3 is a bottom, non-perspective view of one aspect of an apparatus of this invention 1 for exercising a human's foot or ankle.

Referring now to FIG. 2, one sees a side, non-perspective view of one aspect of an apparatus of this invention 1 for exercising a human's foot or ankle. The base frame 2 is adapted to sit in a stable position on a floor. A horizontal bar 3 (not shown in FIG. 2) is positioned above the base frame and is connected to a vertical assembly 4 connecting the horizontal bar 3 to the base frame 2. The vertical assembly 4 is shown in FIG. 2 connecting the base frame to the upper horizontal bar 3 at about a 45 degree angle with another portion of the assembly 20 being 90 degrees to the base frame. For stability, it has been found that the vertical assembly is attached to three of the four sides of the base frame, as can be seen in both FIGS. 2 and 3. As can be seen in FIGS. 2 and 3, the vertical assembly comprises at least two arms attached to opposite first and second sides of the base frame and at least two arms attached to the third side of the base frame, wherein each of the arms of the vertical assembly is attached to the horizontal bar.

A platform 5 is positioned between the horizontal bar 3, vertical assembly 4, and base frame 2, said platform 5 having an upper side 6 and a lower side 7; the upper side 6 has a forefoot region 8 and a heel region 9 for receiving a human foot. A support member 10 pivotably engages with the lower side 7 of the platform 5 through an extension and is attached to the base assembly 2. As mentioned before, the junction of the extension from platform 5 and base frame 2 allows for the pivotable engagement of the two so that the platform 5 can rotate relative to the base frame in all 3 axes, X, Y, and Z. This readily accomplished using a universal joint or a ball joint connection that allows the platform 5 to pivot in all six directions. An upper resistance means 11 connects between an attachment 12 on the underside 7 of base 5 to an attachment 16 positioned above the platform and connected to the horizontal bar 3 or the vertical assembly 4. A lower resistance means 13 secures an attachment means 14 connected to the platform 5 to an attachment means 15 connected to the base frame 2.

The base frame 2 may be made from a single piece of material such as plastic, metal, wood, or similar material that is stable and rigid. In the aspect shown in FIG. 2 and other Figures in this application, the base frame 2 is made of a tubular plastic such as furniture grade PVC and employs T joints 27 to connect to the vertical assembly 20, which in turn connects to the upper horizontal bar 3 by T joints 19. Additional vertical connectors 20 provide greater stability for the apparatus. The corners of the base may be connected using T joints 27 that are common in the art, while L joints 21 may be used to connect vertical pieces 20 to the horizontal bar 3.

Figure 5:
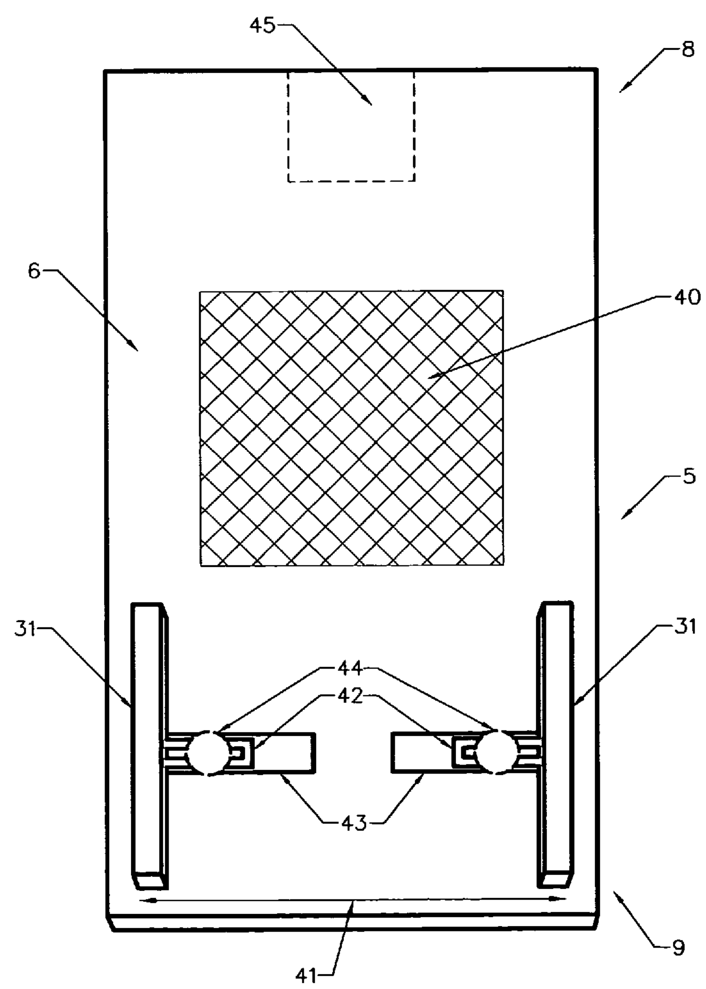
FIG. 5 is a top, detail view of a platform to accept the foot being exercised using the apparatus of this invention.

The upper surface 6 of platform 5 may be smooth or preferably may further comprise a non-skid textured surface. The upper side 6 of the platform 5 may further comprises at least one strap 23 for securing the foot to the platform 5. Such strap is preferably adjustable and may employ a hook and loop fastener (e.g., Velcro brand) to aid in securing the foot the platform or may employ a buckle 24 as shown in FIG. 1 or other type of fastener such as a button, snap or other similar devices useful for securing the foot to the platform. The upper surface 6 may also include a heel stop 22 at the heel region 9 of platform 5 for limiting the motion of the heel relative to the platform. The heel stop may simply be a ridge integral with or attached to platform 5 as shown in FIG. 1 or may be two parallel ridges 31 on the right and left side of the platform 5 as shown in FIGS. 4 and 5.

A resistance means useful in the apparatus of this invention may be any means that provides resistance to a particular movement when employed in the device of this invention. As shown in FIG. 2, the means 11, 13, and 25 is simply a stretchable band made of a plastic, rubber, or the like. In operation the user can strengthen her or his ankle by placing a foot onto the platform of the exercise apparatus and flexing the foot in any of six directions against the resistance provided by the apparatus. The user can stand or sit while doing the exercise. In either case it may be useful to include foot rests 30 for receiving a left or right foot that is not being exercised, wherein the foot rests are attached to or are integral with the base frame. To aid the user if he or she wishes to stand while exercising the apparatus may include vertical, transverse arms spaced parallel to one another (not shown in FIG. 2) and attached to the base frame at one end and a handle at the other end for receiving a user's hand to assist in balancing when the apparatus is in use.

Referring now to FIG. 3, one sees a bottom, non-perspective view of one aspect of an apparatus of this invention 1 for exercising a human's foot or ankle. The numerals used in this description are the same as those used for FIGS. 1 and 2. The base frame 2 is adapted to sit in a stable position on a floor. The base frame shown here comprises four integrally connected bars defining a rectangular shape and a crossbar bisecting the base frame. A horizontal bar 3 is positioned above the base frame and is connected to a vertical assembly 4 connecting the horizontal bar 3 to the base frame 2. The vertical assembly 4 is shown in FIG. 3 connecting the base frame to the upper horizontal bar 3 at about the same 45 degree angle as in FIG. 2, but from the bottom perspective and can't be seen to show the angle connection. A platform 5 is positioned between the horizontal bar 3, vertical assembly 4, and base frame 2, said platform 5 having an upper side 6 (not shown in FIG. 3) and a lower side 7; the upper side 6 has a forefoot region 8 and a heel region 9 for receiving a human foot, not shown. A support member 10 pivotably engages with the lower side 7 of the platform 5 and is attached to the base assembly 2. The support member 10 connects to the platform 5 through a universal or ball joint that allows the platform 5 to pivot in all six directions as discussed above. An upper resistance means 11 (not shown in FIG. 3, but seen in FIGS. 1 and 2) connects between an attachment 12 on the underside 7 of base 5 to attachments 16 positioned above the platform and connected to the horizontal bar 3 or the vertical assembly 4. A lower resistance means 13 (again, not shown) secures an attachment means 14 connected to the platform 5 to an attachment means 15 connected to the base frame 2.

As discussed before, the base frame 2 may be made from a single piece of material such as plastic, metal, wood, or similar material that is stable and rigid. In the aspect shown in FIG. 3 and other Figures in this application, the base frame 2 is made of a tubular plastic such as furniture grade PVC and employs T joints 27 to connect to the vertical assembly 20, which in turn connects to the upper horizontal bar 3 by T joints. Additional vertical connectors 20 (not shown in this FIG. 3) provide greater stability for the apparatus. The corners of the base may be connected using T or L joints that are common in the art.

The upper surface 6 (not shown) of platform 5 may also include a heel stop 22 at the heel region 9 of platform 5 for limiting the motion of the heel relative to the platform.

Referring now to FIG. 4, one sees a perspective view of one aspect of an apparatus of this invention 1 sitting in a stable position on a floor. A horizontal bar 3 is positioned above the base frame and is connected to a vertical assembly connecting the horizontal bar 3 to the base frame as discussed in the previous figures. The vertical assembly is shown in FIG. 4 connecting the base frame to the upper horizontal bar 3 at about the same 45 degree angle as in FIG. 2. A platform 5 is positioned between the horizontal bar 3, vertical assembly, and base frame, said platform 5 having an upper side with a forefoot region and a heel region for receiving a human foot, not shown. The upper surface of platform 5 is shown having a non-skid textured surface. The upper side of the platform 5 in this aspect is shown to have two parallel ridges 31 for positioning the heel of the user on the upper surface of platform 5 and further comprises at least one strap for securing the foot to the platform 5. The ridges aid in the securing and positioning of the heel on the platform and may be laterally adjustable to accept a variety of foot sizes and heel widths. A support member pivotably engages with the lower side of the platform 5 and is attached to the base assembly 2, as discussed hereinbefore. The support member connects to the platform 5 through a universal or ball joint that allows the platform 5 to pivot in all six directions as discussed previously. An upper resistance means connects between an attachment at the forefoot region of base 5 to an attachment positioned above the platform and connected to the horizontal bar 3. Other resistance bands are shown to be attached to the vertical assembly.

As discussed before, the base frame 2 may be made from a single piece of material such as plastic, metal, wood, or similar material that is stable and rigid. In the aspect shown in FIG. 4 and other Figures in this application, the base frame 2 is made of a tubular plastic such as furniture grade PVC In operation the user can strengthen her or his ankle by placing a foot onto the platform of the exercise apparatus and flexing the foot in any of six directions against the resistance provided by the apparatus, as discussed previously. It may be useful to include right and left foot rests 30 for receiving a left or right foot that is not being exercised, wherein the foot rests are attached to or are integral with the base frame. To aid the user if he or she wishes to stand while exercising the apparatus may include vertical, transverse arms 32 spaced parallel to one another and attached to the base frame at one end and a handle 33 attaching the vertical arms 32 at the other end for receiving a user's hand to assist in balancing when the apparatus is in use.

Turning now to FIG. 5, one sees a detail of the platform 5 of this invention. As discussed previously with reference to FIGS. 1-4, a platform 5 is positioned between the horizontal bar 3, vertical assembly 4, and base frame 2, said platform 5 having an upper side 6 and a lower side 7 (not shown in this FIG. 5); the upper side 6 has a forefoot region 8 and a heel region 9 for receiving a human foot onto the upper side 6. A support member 10 (not shown in this FIG. 5) pivotably engages with the lower side 7 of the platform 5 and is attached to the base assembly 2. The pivotal engagement allows for rotation of the platform 5 in the X, Y, and Z axes of the apparatus. The shape of the platform 5 will generally be elongate with the length running from the heel region 9 to the fore foot region 8 and is of a length and width sufficient to accept various sizes of a human foot. The dimensions may vary to be useful for exercising a child's foot/ankle to a professional basketball player's foot/ankle. One will recognize that the size of the platform may vary significantly for the target audience. The length may vary from less than a foot to more than 2 feet, with the length being greater than the width. While the platform shown in FIG. 5 is rectangular, it is understood that the platform could be designed with rounded or even relatively pointed ends. The upper surface 6 of platform 5 may be smooth or preferably may further comprise a non-skid or textured surface shown in FIG. 5 as the cross hatched area 40. The upper surface 6 of the platform 5 may further comprise at least one strap, not shown here, for securing the foot to the platform 5. Such strap is discussed hereinbefore. The upper surface 6 may also include a heel stop shown as 22 in FIGS. 1-3 at the heel region 9 of platform 5 for limiting the motion of the heel relative to the platform. The design of the heel stop may be a ridge as shown in FIG. 1 or may be of a design shown here and in FIG. 4. The heel stop is used to secure the heel to the upper surface 6 of platform 5 and prevent the heel from moving laterally or medially doing the exercises using the apparatus of this invention. Here the heel stop is shown to be 2 parallel ridges 31, which may be permanently affixed to the surface 6 of platform 5. In this case the parallel ridges are adjustable laterally and medially in the direction of arrows 41. This sideways adjustment can be accomplished using ridges 31 having extensions 42 that are designed to fit in grooves 43 in the surface 6 of platform 5 so that the upper surface of extension 42 is level with surface 6. Screws 44 (shown with dotted circles) fitting into recessions in the platform 5 can be tightened to secure the ridges 31 to the platform to prevent sideways motion and can be loosened to allow the ridges to be adjusted to the desired width of the foot being exercised. Thus one can see that the heel stop of this invention may be located at the end of heel region 9 as shown in FIGS. 1-3 or may be two ridges opposing each other, between which a user's heel can fit. In either case the heel is prevented from moving laterally, medially, and generally longitudinally.

How to Make an Article of Manufacture of this Invention

In making the device described herein. One of ordinary skill will recognize numerous pathways can be taken to prepare a final product. The following discussion sets forth an exemplary method for production. This description of making the apparatus of this invention will be limited to detailed description of the invention as displayed in the FIGS. 1-5. It will be recognized by one of ordinary skill that numerous other methods could be used to prepare equivalent devices.

The base frame is adapted to sit in a stable position on a floor and is generally a four sided base, although it may be three or more that four sides. Because of ease of preparation the base is of a square, trapezoidal, or rectangular shape, preferably the latter. The dimensions may be about 2-4 feet by 2-4 feet, depending on the stability desired and the space requirements of the user. The base is generally made by cutting lengths of standard furniture grade PVC pipe to the desired lengths, connecting them to each other using "T," "L" or other linear connectors to make the design shown in FIGS. 1-4. T connectors are shown in FIG. 1 as numerals 17 and 19 while L connectors are shown as numerals 21 and 18. The base is assembled first with the vertical assembly 4 being added thereto so that it can then be attached to the horizontal bar 3 positioned above the base frame 2. The support member 10 shown in FIG. 3 is integrated into the base frame so that it pivotably engages the platform 5 through a universal or ball joint that allows the platform to swivel so that the user can move the foot placed on the platform throughout all planes of motion to exercise the muscle discussed above. Prior to or after connecting the platform 5 to the support member 10, the platform is fitted with the optional heel restraint 22, ridges 31, the non-skid textured surface, and strap 23 along with resistance connectors such as 12, 14, and 15. Resistance connectors 16 are then placed on the horizontal bar 3. Once all parts are assembled as discussed, the T, L, and linear connectors may be secured with appropriately sized screws 34 to further stabilize the apparatus. Finally, the resistance bands are added to the apparatus to prepare it for use by the person doing the exercise, whether simply strengthening rehabbing after an injury.

As discussed in greater detail hereafter, the device of this invention can be combined with a sensing device that senses the motion of the device of this invention and communicates the results of the motion to the user. Such a sensing device is discussed below and may be placed on the platform 5 by inserting it into a recession 45 where it detects the movement of the fore foot region of the platform and communicates the extent of that movement to the user to determine if the displacement is complete and the exercise is being performed properly.

A Combination with a Sensor

Having explained certain physical characteristics of the invention by referring to FIGS. 1-5, another aspect of the invention is the combination of the article of manufacture discussed herein with a sensing device that senses the motion of the device of this invention and communicates the results of the motion to the user. With this information so communicated, the user can be informed that he or she is doing the exercise correctly. The communication may be visually, audio, or some other means of informing the user of the work being done and whether it is correct. Usually this will require a sensor with a transmitting module and a receiving module to track the information and display and store it. This combination is particularly useful for the user to track his or her progress towards the goal that might be set by a user, trainer, physical therapist, doctor, caregiver, or support group to track the progress of the user over time.

Such a combination is an article of manufacture, as described hereinbefore, with motion sensor that allows for the measurement of the number of movements of the platform 5 relative to a stationary position when used and a receiver that allows for the transmission, display, and storage of such measurement. Such a sensor and receiver combination can be viewed as similar to a cyclometer, which is a device that counts the number of rotations a bike pedal goes around and accumulates the number for the user to track. In essence it is a motion sensor and a data collecting device that may be mechanical or electronic. The sensing mechanism may employ optical, magnetic, electronic, infra red, ultrasonic, microwave, radio frequency, or other technology. In a simple exemplary operation a magnet is attached to the article of manufacture at the toe end 8 of the platform or any other part of the platform 5 shown in FIGS. 1-5. A traditional magnetic sensor, which may be based on the Hall Effect or on a magnetic reed switch, is attached to the body of the ankle exercise device along the upper horizontal bar, the vertical assembly, or the base being used in a position to detect when the magnet of the platform moves away from or towards the stationary sensor. The information is transmitted to display the number of movements of the platform and the distance moved from the stationary sensor. Such transmission may be done using a wired connection or a wireless connection. Speed of movement can be calculated from distance against a lapsed time period. The information can be displayed and collected to be transmitted by visual or other observation or by wireless data transmission to the user and others as part of the training and rehab program for the user. Other information, such as heart rate, may also be integrated into the system. A manufacturer that that makes cyclometers that may be adapted for this purpose is CATEYE©. Another company is Velocomputer™. Others will be apparent to one of skill in the art having read this information provided in this patent application. Alternatively, applications are available and readily modified for cell phone or iPhone or iPod Touch use that can be used, such as FitFu. In such a case the iPhone could simply be strapped to the foot of the user and by using the accelerometer the application would track the results and transmit the results to the user, a trainer, physical therapist, doctor, caregiver, or others for support and progress tracking. Tracking the results is important in ensuring that the user is really doing the exercise. It has been shown in many studies that repetition is necessary to retrain the brain and the body to accelerate the recovery and strengthening process.

An example of a combination of the article of manufacture discussed herein referring to FIGS. 1-5 with a sensing device that senses the motion of the device of this invention and keeps track of the work being done by the user is now provided. This combination is particularly useful for the user to track his or her progress towards the goal that might be set by a user, trainer, physical therapist, doctor, caregiver, or support group to track the progress of the user over time. The combination measures dorsiflexion/plantar flexion and pronation/supination degrees of displacement. The measured values are displayed on a computer (using in LabVIEW discussed below) or on a LCD or other visual or audio display. In order to display the degree displacement on the LCD display a three-axis accelerometer is used along with an Atmega328 chip, which is programmed with the Arduino IDE. In order to display the degree of displacement on a computer screen a three-axis accelerometer is also used in accordance with an Atmega328 and National Instruments PCI-6024E multifunction DAQ board, where the program code is created in LabVIEW 8.2. The measured values in this description are displayed both on the LCD and the Lab View Front Panel on a value from −10 to 10. One of ordinary skill in the art will recognize other options are available falling within the scope of disclosure in this application.

Figure 8:
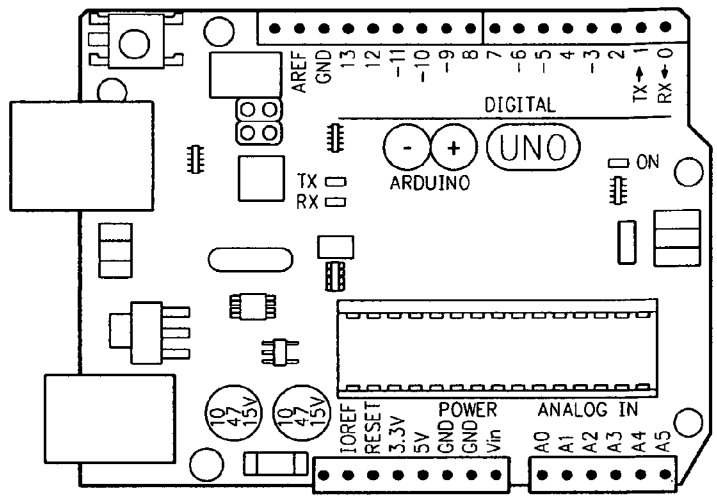
FIG. 8 is an image of the Arduino Uno Hardware, a board into which the AtMega328 microcontroller is integrated.
Figure 9:
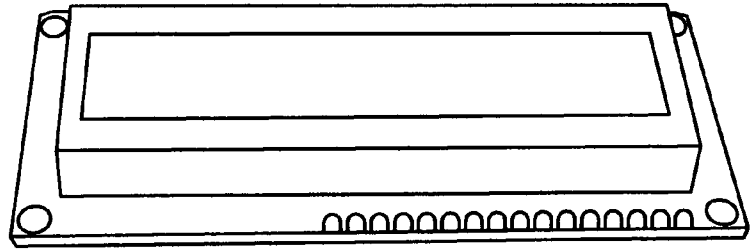
FIG. 9 is an image of a representative LCD display, the Longtech Optics LCM1602A 2×16 alphanumeric display, useful as a readout to communicate the number of repetitions done by the user of this invention.
Figure 10:
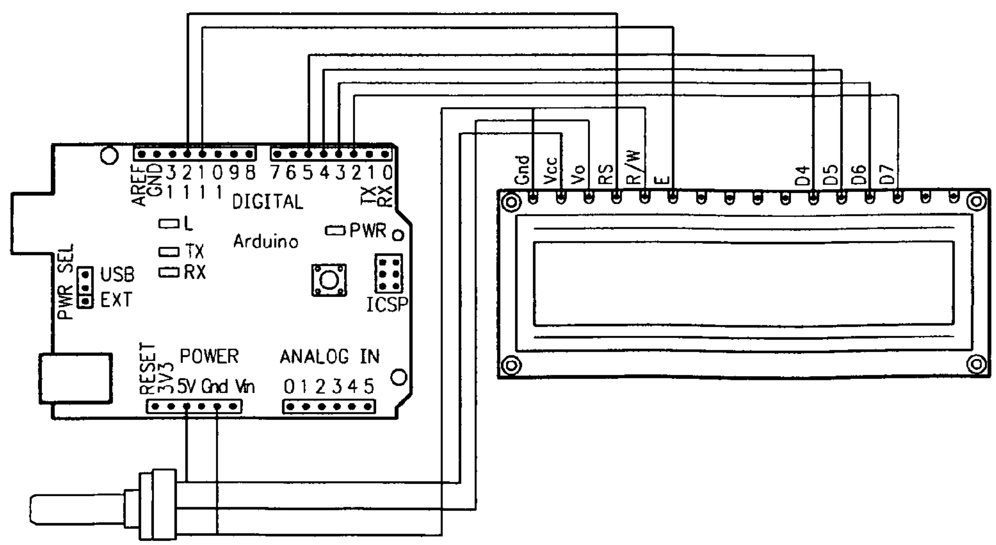
FIG. 10 is a diagram that explains how to hook the display of FIG. 9 to the Arduino board of FIG. 8.
Figure 11:
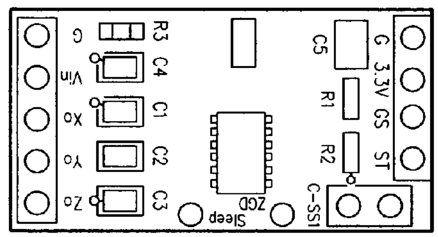
FIG. 11 is a depiction of the three-axis accelerometer MMA7361 positioned on a break out board that is connected to the Arduino board wire G and V in on the accelerometer to ground and 5 volts on the Arduino respectively.

An appropriate accelerometer for use in this aspect of the invention is a MMA7361 three axis accelerometer, which is available from numerous commercial sources in the US and internationally, and measures static or dynamic forces applied to the platform 5 of the device shown in FIGS. 1-4. The schematic of the MMA7361 accelerometer is shown in FIG. 6. A microcontroller, which is a small computer that contains a processor core, memory, and programmable inputs and outputs, is used with the accelerometer. A useful microcontroller for this purpose is the Atmel Corporation AtMega328, which is programmed by the Arduino integrated drive electronics. A schematic of the microcontroller is shown in FIG. 7. The Arduino Uno hardware is a board for the Atmega328. The Uno has every component to support the Atmega328; to power the Uno one must connect the Uno via a USB cable or use an ac to dc adapter. FIG. 8 has an image of the Arduino Hardware. The Arduino Uno is the brains behind the combination invention discussed in this section of this patent application. The AtMega328 Micro-controller is the hub of all the input and output of the invention. In this discussion a standalone device is described using an LCD display such as a Longtech Optics LCM1602A 2×16 display as shown in FIG. 9. The diagram in FIG. 10 explains how to hook the display to the Arduino board. To use the backlight of the display the LED− is wired to ground and LED+ to 5 volt source with a current limiting resistor in line. To measure the displacement of the device the three-axis accelerometer MMA7361 is positioned on a break out board. The board is displayed in FIG. 11 and is connected to the Arduino wire G and V in on the accelerometer to ground and 5 volts on the Arduino respectively. Then wire Xo and Yo on the accelerometer is connected to analog pins A0 and A1 respectively. The rest of the pins on the breakout board are not needed.

Figure 12:
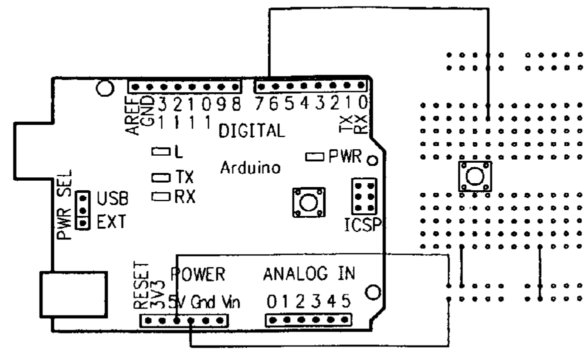
FIG. 12 is a pushbutton schematic to change the mode of the device.

It is also necessary to hook up a pushbutton to change the mode of the device. The wiring diagram for this is shown in FIG. 12. The Arduino reads pin 7 to see if the button is being pushed. The final part of the hardware is to connect the Arduino to the National Instrument (NI) data acquisition (DAQ). This is just two simple connections: connect Arduino's pin 9 to the DAQ's Ai1 and ground to ground. The complete wiring diagram can be seen in FIG. 12.

Figure 13:
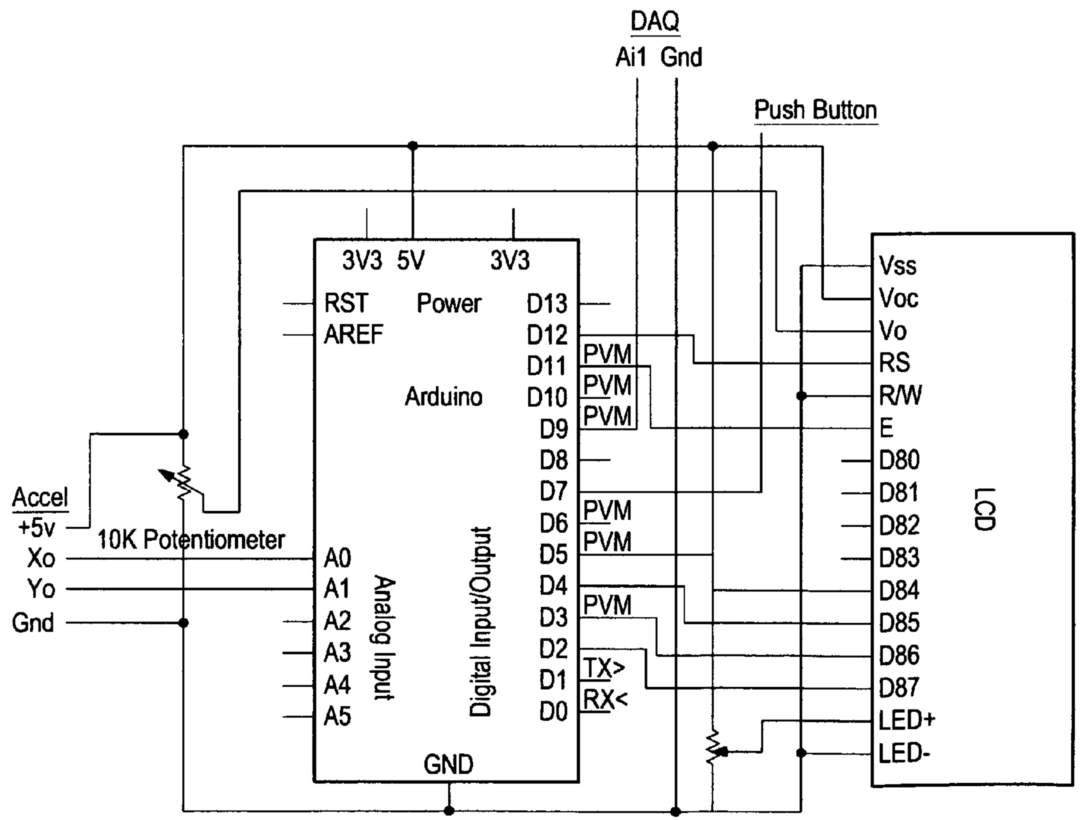
FIG. 13 is the overall wiring diagram for the Arduino board and the LCD display.
Figure 14:
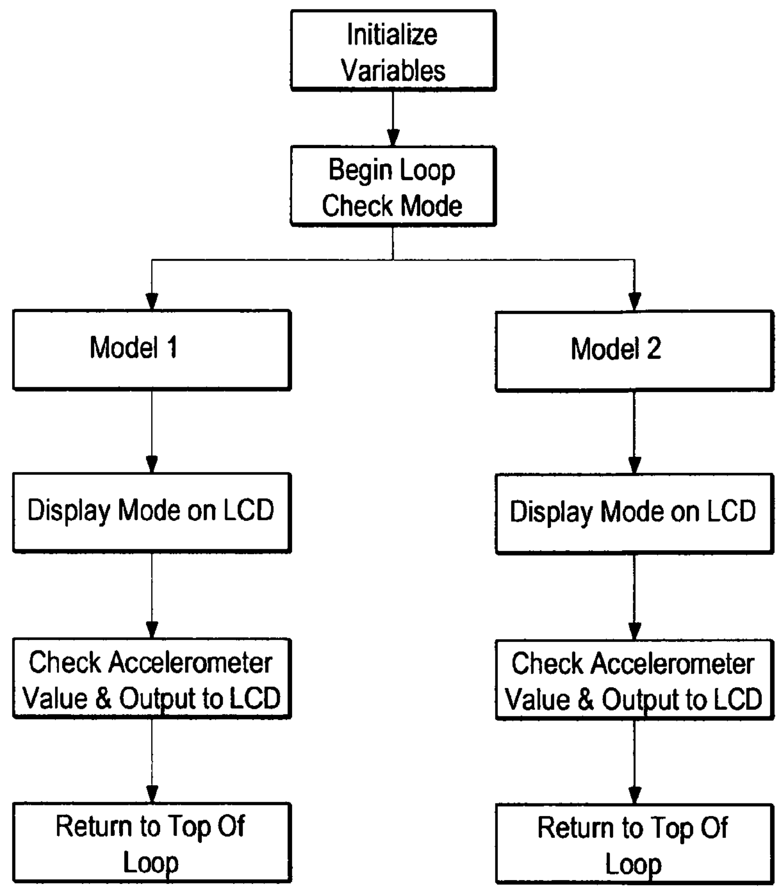
FIG. 14 is a code flow chart that depicts the underlying essential concepts to the Arduino code for integrating the sensor into the invention.

The flow chart displayed below in FIG. 13 depicts the underlying essential concepts to the Arduino code. Beginning with the initialization of global variables (such as integers representing the mode selected, the button presses, and accelerometer values), the code sets the pins to either receive or send signals and the LCD display to activate the welcome message.

Once the setup is completed, the code begins the loop that governs the main automation of this aspect of the invention. Again the required variables are initialized, and the first check the loop performs is to verify which respective mode the current device is under. This mode determinate is stored under an integer value as either 1 or 0 (with 0 representing Dorsi/Plantar and 1 representing Pro/Supination). With the proper mode setting, the code sends signals to the LCD to display, which respective mode it is in as well as the accelerometer value the code is receiving. The accelerometer values received by the Arduino are fairly noisy, so several if functions were implemented filter and average the values. This results in a cleaner output as well as a smoother data feed. In addition, another signal is sent to the DAQ via a tone function, which allows more reliably interpreted data being collected by the Arduino through LabVIEW, as discussed below. When this step has been completed the code returns to the top of the loop and the process begins anew.

The tone function used to transmit data to the DAQ (via digital pin 9 on the Arduino). The tone function is a square wave transmitted at a specified frequency (and at 50% duty cycle), e.g., between 100 and 1000 hertz depending on the accelerometer value being received by the Arduino. This allows the DAQ interfaced with LabVIEW to properly interpret the data transmitted by the Arduino. Syntax for the tone function used in the code used is as follows: tone (pin, frequency) where 'pin' denotes which pin is wanted to output on and 'frequency' would be the frequency of the signal sent.

The LCD display interfaced with the Arduino board is connected via digitals pins 2, 3, 4, 5, 11, and 12. Pins 2 to 5 serve as character defining pins while pins 11 and 12 serve as the enable and RS pins respectively. Arduino's built in LCD library allows an easily defined display to depict without any hassle or tedious bit crunching. As for the accelerometer, only two analog pins were required in order to receive the data needed to calculate the respective position of the foot pedal platform 5.

To create a more robust product with options of a user-friendly computer interface, a separate program using LabVIEW is useful. LabVIEW is short for laboratory virtual instrumentation engineering workbench and is a system design platform and development environment for a visual programming language from NI. Although the LCD screen provides fair visualizations of a user's inputs, use of this LabVIEW VI allows them an easier way of tracking their motion. Unlike the Arduino-based LCD monitor, the VI is displayed on a computer monitor and makes use of the extra space by including larger, clearer buttons and displays.

To create the VI, LabVIEW 8.2 is used on the appropriate computer available to one of ordinary skill in the art. The basic structure of the VI can be created by one of ordinary skill in the art using a State Machine, which is a mathematical model used to design computer programs and digital logic circuits. The primary characteristics of a state machine are quite similar to that of cases used in common programming. User input or results from previous states are used to control which state the VI is in. Each state contains a separate program making quick work out of what could be a complex programming situation. This state machine architecture is most common in creating user interfaces which makes it useful in carrying out the invention described in this application.

Figure 15:
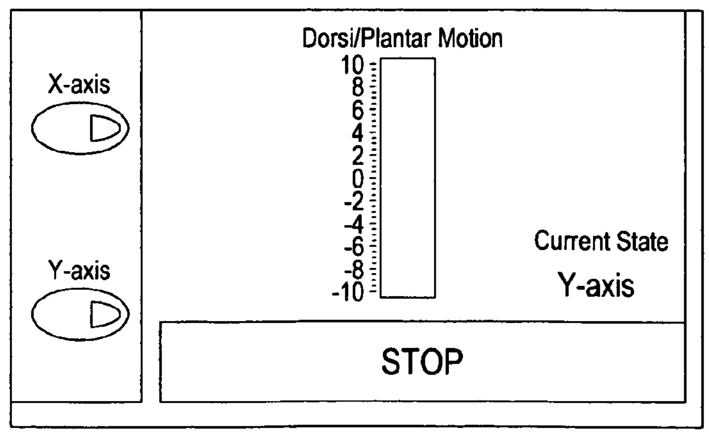
FIG. 15 is a front panel of a computer interface useful in this invention that allows the user to choose controls and indicators for performing the various modes of exercises described herein.
Figure 16:
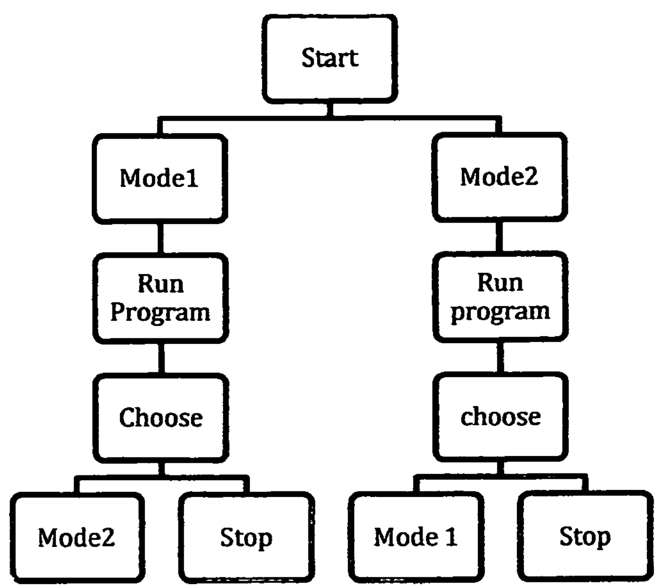
FIG. 16 is a flow diagram that provides flow of a program to run the interface.

The first step in creating this VI was to build the front panel for visualization on a computer screen. The front panel is the user interface that provides the user with the ability to choose controls and indicators that are both appealing and easy to interpret. For this VI, three control buttons may be used for either mode and to stop the program. A representative interface is depicted in FIG. 15 showing the dorsi/plantar motion along the Y axis. Along with these buttons are two slide indicators showing the user's movement; either forward and back or side to side showing a scale of positive 10 or negative 10. The indicators of course correspond to the mode in which the user chooses. Lastly, a display indicator shows what state/mode the program is in. Once the front panel of the VI is completed, construction of the block diagram can begin. In this new block diagram all indicators and controls created in the front panel are visible. The next part in creating the VI was to create a state machine. To obtain a better understanding of what the program does, a block diagram is provided in FIG. 16 to show the basic flow. As can be seen in the block diagram, the user can choose which mode to run and once in that program they can then choose to switch modes or stop the program all together. As long as the user does not stop the program they can continue to switch back and forth between the two modes.

The state machine represented here has 4 states; initialize, state 1, state 2, and stop. In the initialize state, the user is prompted to choose which mode. From there state 1 or state 2 is opened. In each of these states a second case structure (state machine) is created to allow the user to switch between states or stop the program. To create the "outer" state machine, create a while loop and place a "case structure" inside that loop. The "Standard State Machine" template provided in LabVIEW is a good starting point for developing the block diagram. In the "Initialize" state, create a dialog window that prompts the user to select an axis. Then based on that choice it triggers the shift register to switch states. Along with the dialog box, connect the three control buttons and the "current state" indicator box to the case structure. Having provided the foregoing detailed information, one of ordinary skill can make and use the various aspects of the invention described.

The invention described in this application also relates to additional devices, systems, and processes for assisting human users in performing rehabilitation and strengthening exercises using the ankle exercise and strengthening device of this invention after an incident results in an injury or condition that requires such rehab exercises for the person to work his or her way back to pre-incident physical condition.

In a broad aspect, our invention can be viewed as an article of manufacture for aiding a human user participating in a foot or ankle exercise program. The article comprises (a) a sensor associated with an device as discussed in relation to FIGS. 1-5 and that senses the position or movement of the foot on the platform of the device in use and produces data regarding the exercise that is communicated to the user, optionally with (b) an electronic device for transmitting such data to a data receiving device that can store and process such data. It is particularly useful if the receiving device communicates with a browser-based web service or client-server application interface that optionally allows the user to access an instructional data base that is specific to the type of rehab program for the user to aid in performing the user's exercise program. In addition to (a) and (b) another aspect is to include (c) a browser based web service or client-server application interface to allow the user to evaluate information about the progress of his or her rehab exercise program. The article can be designed so that the sensor can be associated with the foot of the user being exercised in the user's exercise regimen. It is found to be particularly useful wherein the application interface of (c) allows sharing of information with a support network, for example when the interface of (b) or (c) includes the ability to inform a caregiver, trainer, or health professional. The article of manufacture of this invention lends itself well to a rehab program wherein each movement of the foot on the platform is associated with a training video and/or other visual aid to assist the user in his or her strengthening or recovery program. Such visual aids can include video, audio, written material, on line flash cards, and other types of information transmission to guide the user through the recovery process.

Another aspect of this invention is an article of manufacture, i.e., a device, for aiding a human user participating in a rehab or strengthening exercise program. The device comprises (a) a sensor is associated with the ankle exercise device and that senses the position or movement of such device in use and produces digitized data regarding the exercise. The sensor is combined with (b) a device for transmitting such data to a data receiving device or apparatus (e.g., a mobile phone) that can store and process such data, wherein the receiving device communicates with a browser-based web service or client-server application to send such data to a medical professional or caregiver overseeing the well being of the user through a feedback web based or client server application interface that allows the medical professional to view the received exercise data and communicate feedback directly to the user. Components (a) and (b) are then used with (c) a browser based web service or client-server application interface to allow the user to access a database of exercise protocol guidelines, how to videos, guidelines and strategies that go along with each stage of recovery and/or to share information about the progress of his or her rehab exercise program with a social network support group to compare progress and obtain feedback from the support group. The sensor senses the exercise movement using standard technology such as a gyroscope or accelerator mechanism, as discussed above, and may be associated with a connector that allows the sensor to be connected to the foot of the user being exercised or the exercise device. The sensor can be associated with a user interface for collecting movement data with a self reporting dashboard and/or calendar. The device for transmitting the exercise data employs a short range communication protocol (SRCP) such as Bluetooth or Ant brands. The data that is sent to the user, caregiver, trainer, and/or medical professional is preferably encrypted using standard encryption mechanisms to protect confidential medical patient information.

Another aspect of this invention is device or article of manufacture for aiding a human user participating in a rehab exercise program, which article comprises (a) a sensor that can be associated with the foot of the user being exercised with an exercise device as discussed in relation to FIGS. 1-5 and that senses the position or movement of such foot in use and produces digitized data regarding the exercise, (b) a device for transmitting such data to a data receiving device that can store and process such data, wherein the receiving device communicates with a browser-based web service or client-server application to send such data to a trainer, medical professional, or caregiver overseeing the well being of the user through a feedback web based or client server application interface that allows the trainer, etc. to view the received exercise data and communicate feedback directly to the user, and (c) a browser based web service or client-server application interface to allow the user to access a database of exercise protocol guidelines, how to videos, guidelines and strategies that go along with recovery and share information about the progress of his or her rehab or strengthening exercise program with a social network support group to compare progress and obtain feedback from the support group.

Another aspect of this invention comprises (a) an apparatus as described above in the discussion of FIGS. 1-5 for assisting the user in the user's exercise program (b) a sensor that can be associated with such apparatus and that senses the position or movement of such apparatus in use and produces digitized data regarding the exercise, (c) a device for transmitting such data to a data receiving device that can store and process such data, wherein the receiving device communicates with a browser-based web service or client-server application to send such data to a trainer, medical professional or caregiver overseeing the well being of the user through a feedback web based or client server application interface that allows the medical professional to view the received exercise data and communicate feedback directly to the user, and (d) a browser based web service or client-server application interface to allow the user to access a database of exercise protocol guidelines, how to videos, guidelines and/or strategies that go along with recovery and/or to share information about the progress of his or her rehab exercise program with a social network support to compare progress and obtain feedback from the support group.

A Process for Making an Article of Manufacture of this Invention

Another aspect of this invention is a process for making an article of manufacture for aiding a human user participating in a rehab exercise program, which process comprises a) combining the apparatus discussed above relative to FIGS. 1-4 with b) a sensor that can be associated with such apparatus and that senses the position or movement of such adaptive apparatus in use and produces data regarding the exercise and transmits such data to a data receiving device that can store, display, and/or process such data, wherein the receiving device optionally communicates with a browser-based web service or client-server application to send such data to a trainer, medical professional or caregiver overseeing the well being of the user through a feedback web based or client server application interface that allows the trainer, etc. to view the received exercise data and communicate feedback directly to the user, and wherein the data receiving device communicates with a browser based web service or client-server application interface to allow the user to share information about the progress of his or her rehab exercise program with a social network support group to compare progress and obtain feedback from the support group.

Having read the foregoing description, one can perceive another process aspect of this invention. It is a process for of manufacture of an apparatus for exercising a human's foot or ankle, which process comprises the following steps that may be performed in any order, but that satisfactorily are performed in the order set forth below. The process comprises a) providing a base frame adapted to sit in a stable position on a floor;

b) providing a horizontal bar for positioning above the base frame;

c) connecting a vertical assembly to the horizontal bar and to the base frame;

d) positioning a platform between the horizontal bar, vertical assembly, and base frame, said platform having an upper side and a lower side, the upper side defining a forefoot region and a heel region for receiving a human foot;

e) attaching a support member to the base frame assembly in a manner to pivotably engage with the lower side of the platform;

f) providing an attachment for a resistance connector to connect the forefoot region of the platform to the horizontal bar and at least two attachments to connect resistance connectors for connecting the lateral and medial sides of the forefoot region to the vertical assembly or base frame, and g) providing an attachment for connecting a lower resistance connector to the heel region of the platform to the base frame. Thereafter, a sensor is associated with the apparatus that senses the position or movement of such device in use and produces data regarding the exercise that is communicated to the user. Other steps may be taken to further combine other aspects described herein with this process.

What is claimed is:

1. An apparatus for exercising a human's foot or ankle, comprising:

a) a base frame adapted to sit in a stable position on a floor;

b) a horizontal bar positioned above the base frame;

c) a vertical assembly connecting the horizontal bar to the base frame;

d) a platform positioned between the horizontal bar, vertical assembly, and base frame, said platform having an upper side and a lower side, (i) the upper side defining a forefoot region and a heel region for receiving a human foot and includes a heel stop for limiting the motion of the heel of the human foot and at least one strap for securing the foot to the upper surface and (ii) the lower side is pivotably engaged through a ball joint to a support member fixed to the base assembly;

e) an upper elastic resistance band for connecting the forefoot region of the platform to the horizontal bar and at least two elastic resistance bands for connecting the lateral and medial sides of the forefoot region to the vertical assembly or base frame;

f) a lower elastic resistance band for connecting heel region of the platform to the base frame and g) two foot rests for receiving a left or right foot that is not being exercised, wherein the foot rests are removably attached to or are integral with the base frame and are positioned to the right and the left of the platform.

2. The apparatus of claim 1, wherein at least two non-skid pads are affixed to the bottom of the base frame.

3. The apparatus of claim 1, wherein the apparatus further comprises a hook to connect the elastic resistance bands to the apparatus.

4. The apparatus of claim 1, wherein a sensor is associated with the apparatus that senses the position or movement of the foot platform in use and produces data regarding the exercise that is communicated to the user.

5. The apparatus of claim 4, which further includes an electronic device for transmitting such data to a data receiving device that can store and process such data.

6. The apparatus of claim 5, which further includes a browser based web service or client-server application interface to allow the user to evaluate information about the progress of his or her rehab exercise program.

* * * * *